United States Patent [19]

Katzenberger et al.

[11] Patent Number: 4,734,309
[45] Date of Patent: Mar. 29, 1988

[54] FORM OF SOLID DIMETHYLTEREPHTHALATE

[75] Inventors: Mark S. Katzenberger, Castle Hayne; Robert E. Michel; Roger G. Rudolph, both of Wilmington, all of N.C.

[73] Assignee: E. I. Du Pont de Nemours and Company, Wilmington, Del.

[21] Appl. No.: 20,090

[22] Filed: Feb. 27, 1987

[51] Int. Cl.⁴ .............................................. B32B 5/02
[52] U.S. Cl. .................................... 428/120; 428/220; 560/77; 560/78; 260/707
[58] Field of Search .................. 428/120, 480; 560/77, 560/78; 260/707

[56] References Cited

U.S. PATENT DOCUMENTS 3,502,711  3/1970  Claybaugh et al. .................... 560/78
3,686,276  8/1972  Slockett ................................ 560/78

FOREIGN PATENT DOCUMENTS 0543370  7/1957  Canada ................................ 560/78

Primary Examiner—Nancy A. B. Swisher
Assistant Examiner—Beth A. Bozzelli

[57] ABSTRACT

A block of dimethylterephthalate having a needle-like crystal structure. The block is easily cleavable, and has a reduced tendency to fuse to other blocks when subjected to bag-stacking pressure.

5 Claims, 2 Drawing Figures

FORM OF SOLID DIMETHYLTEREPHTHALATE

FIELD OF THE INVENTION

This invention relates to solid blocks of dimethylterephthalate (hereinafter sometimes called DMT), having a needle-like crystalline structure.

BACKGROUND OF THE INVENTION

Dimethylterephthalate is a commercially available chemical compound having wide industrial use in the preparation of polyester resins. The polyester resins are used in making textile fibers, plastic bottles, and other molded parts.

Dimethylterephthalate is commercially available in the form of briquets which are made by subjecting granular dimethylterephthalate to heat and pressure. A common dimethylterephthalate briquet of commerce weighs about 9 grams. Such briquets are often packaged for shipping in large bags and the bags are often stacked. Upon opening the bags it is sometimes found that the stacking pressure has caused the briquets to fuse together into a mass that must be fractured before the DMT can be readily processed.

When molten DMT is allowed to cool slowly it forms large flat crystals, and due to zone refining, impurities tend to be concentrated in the area that crystallize last. DMT in the form of large flat crystals remelts slowly. DMT in the form of large flat crystals does not easily cleave, and upon fracture produces undesirable amounts of dust. Briquets made from DMT in the form of large flat crystals retain the slow melting property even if the DMT is partially granulated prior to being formed into briquets.

It is an object of the present invention to produce a form of DMT that has less of a tendency to fuse into a mass when it is subjected to bag stacking pressure. It is a further object of this invention to produce a form of DMT that is more easily melted—i.e., melts more quickly at a given temperature than the usual forms of DMT. It is a further object of this invention to provide a form of DMT that is easily cleavable with low dust production.

SUMMARY OF THE INVENTION

The present invention is a block of DMT having needle-like crystals extending inwardly from all exterior surfaces. The DMT block has a uniform chemical analysis. The block has a maximum thickness of three inches, and the block is easily cleavable into smaller pieces without excessive dusting.

The DMT block of the present invention is achieved by rapidly quenching molten DMT. The quenching can take place by subjecting molten sheets (slabs) of not greater than a three inch thickness to a quenching liquid, e.g., water or ethylene glycol at a temperature from about 0° C. to 30° C. Alternatively, the molten DMT may be poured into suitable molds and the molds quickly cooled, for example, by immersing the molds in a cooling liquid, or if the molds are so equipped, by passing cooling fluid through tubes located in the walls of the mold. As is the case with quenching a molten sheet, the thickness of the DMT in the mold should not exceed about three inches. The three inch limitation is significant in that the heat exchange rate for thicker pieces is insufficient to obtain the desired needle-like cyrstals throughout the block.

DRAWING DESCRIPTION

DETAILED DESCRIPTION

Figure 1:
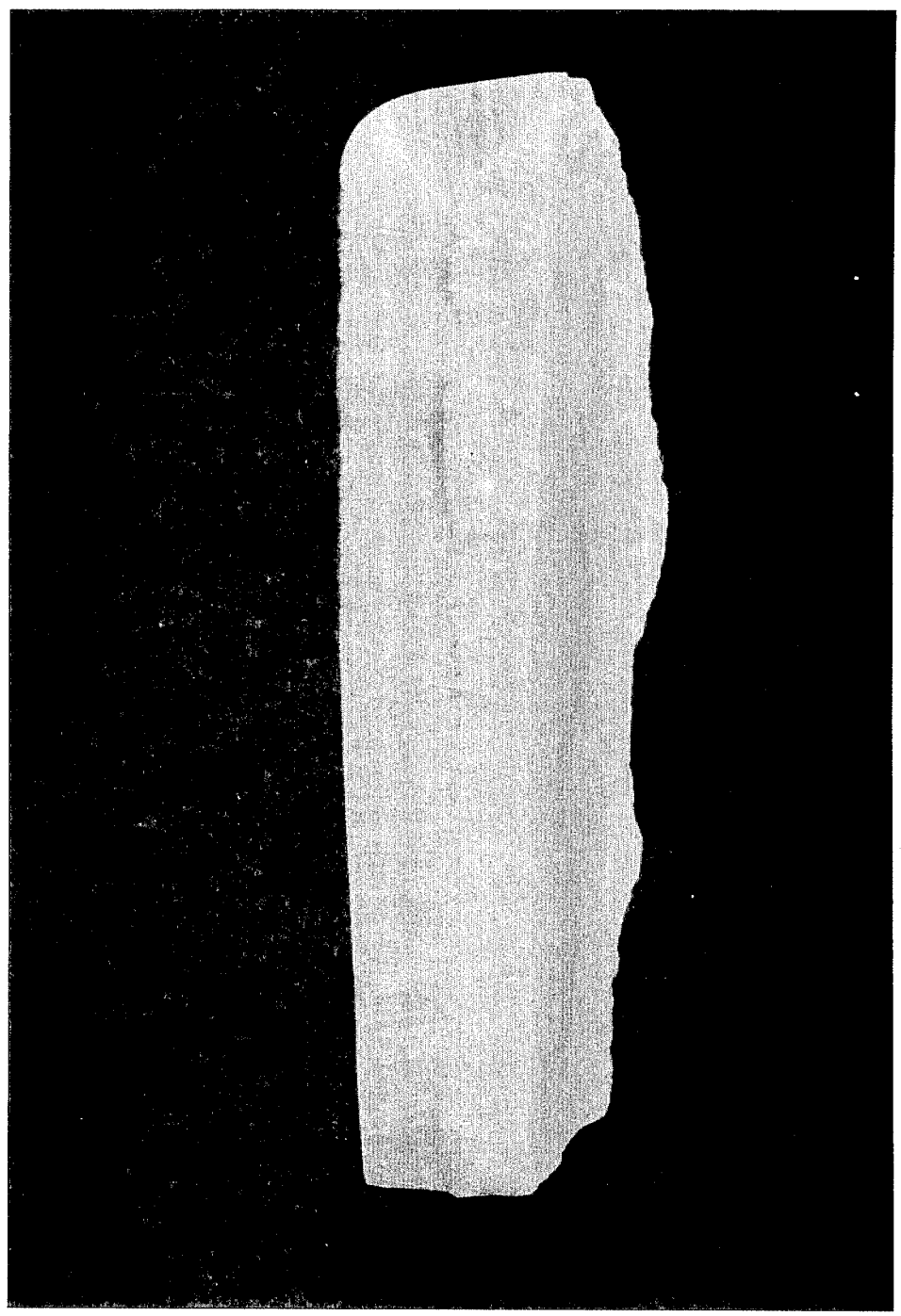
FIG. 1 is a photomicrograph of a cross-section of a block of DMT of the invention.
Figure 2:
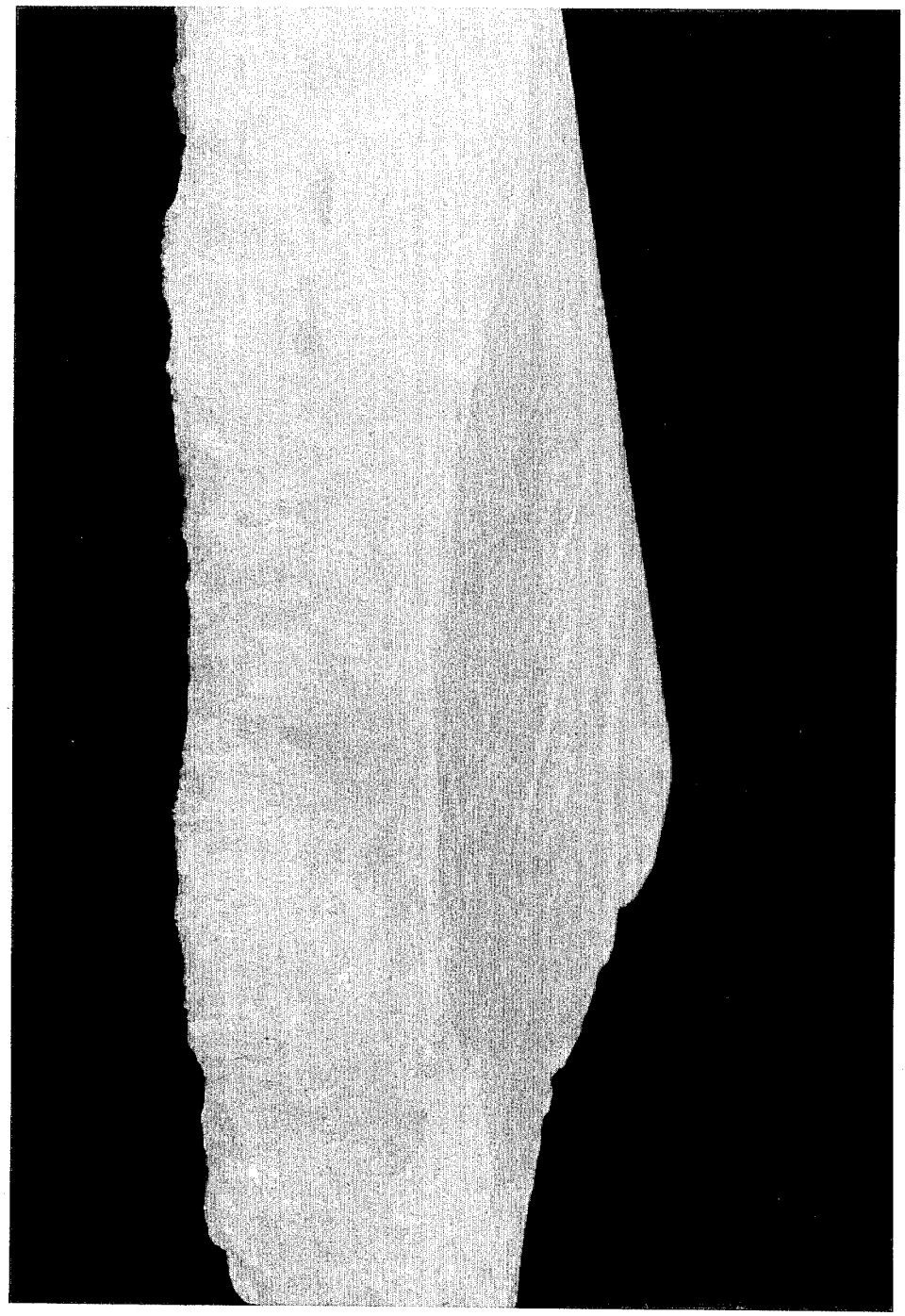
FIG. 2 is a photomicrograph of a cross-section of a block of DMT made by conventional slow cooling of molten DMT.

The DMT block of the present invention is produced by rapidly cooling molten DMT. The rapid cooling causes the DMT to form needle-like crystals that extend inwardly from the exterior of the block. Because of the heat exchange propertes of DMT, a needle-like crystal structure that fills the entire volume of the block can only be obtained on blocks of DMT that are no more than about three inches in thickness—needle-like crystals will extend about one and one-half inches from each surface of the DMT. As shown in FIG. 1, the crystals from opposite surfaces meet in the interior of the block and an optically apparent crystal interruption line forms.

The blocks of DMT of the invention may be made by molding DMT in any shape. The blocks could be cubes, pyramids, rectangular blocks, i.e., blocks of orthorhombic shape, cylinders, toroids or even spheres. For ease in molding, the shape most convenient to produce, would have two substantially parallel oppositely disposed planar surfaces that are separated by a maximum of about three inches; the molding of such shapes would require merely quenching a molten slab of DMT, or the quenching of DMT contained in individual molds where the bottom of the individual mold is flat and the mold is filled with molten DMT while the flat bottom is level. A suitable mold is the shape of a conventional bread pan—a mold with a rectangular flat bottom that is somewhat smaller than its oppositely disposed rectangular opening.

EXAMPLE

Three stainless steel trays having dimensions of a 2 inch height, a 6 inch width and an 8 inch length were employed in this example. Tray 1 was uninsulated. Tray 2 was heavily insulated. Tray 3 was uninsulated and equipped with a lid.

Each tray was filled with molten DMT (145° C.). Tray 1 was placed in an ice-water bath so that only the sides and bottom of the tray were in contact with the ice water. Tray 2 was likewise placed in an ice-water bath so that only the side and bottom insulation on the tray was in contact with the ice water. Tray 3 was immersed in the ice-water bath and ice water contacted the bottom, sides and lid of this tray.

After the DMT in the three trays had solidified the blocks were examined. In the product from Tray 1 there were needle-like crystals extending into the block from the bottom and sides. The center of the top of the block consisted of the usual plate-like micro-crystals of DMT. In the product from Tray 2 there were only plate-like crystals. The product from Tray 3 had needle-like crystals extending inwardly from all exterior surfaces.

The product of Tray 1 could not be cleaved into uniform cubes in the area which contained plate-like crystals. Attempts to cleave the product of Tray 2 into cubes failed and resulted in excessive dusting. The product of Tray 3 was cleaved cleanly parallel to the long direction of the needle-like crystals into cubes.

The cubes of Tray 3 were compared with standard commercial briquets in a melt rate test in ethylene glycol.

Melting rate comparisons between cubed material and commercial briquets were made by placing equal weight samples (9 g) of each in a fine mesh wire basket and immersing the samples simultaneously in an ethylene glycol bath. The samples were approximately of the same gross physical size. The cubes had more surface area since the cube surface is somewhat irregular. Melt time was taken as the time between immersion and disappearance of the solid sample. The results are shown in the following Table.

TABLE

| Run* | Sample | Melt time (sec.) | Bath Temperature |
| --- | --- | --- | --- |
| 1 | briquets | 240 | 154–160° C. |
|   | cube | 220 |   |
| 2 | briquets | 320 | 156–160° C. |
|   | cube | 238 |   |
| 3 | briquets | 330 | 150–160° C. |
|   | cube | 245 |   |
| 4 | briquets | 325 | 156–160° C. |
|   | cube | 255 |   |

Chemical analysis of blocks made by rapid cooling showed no concentration of impurities near the middle of the block, whereas blocks made by slow cooling showed a concentration of impurities near the middle of the block due to zone refining phenomena. The blocks made by rapid cooling had a more uniform melting point, whereas blocks made by slow cooling had a higher melting point exterior and a lower melting point interior.

As a test for resistance to fusion from bag stacking pressure, three layers of cubes of Tray 3 were placed in a metal cylinder and subjected to a pressure of 1 psig for 30 days at 140° F. Upon cooling the cubes were easily removed from the cylinder, and were not fused together.

A similar test using dimethylterephthalate flake resulted in a fused mass.

It is contemplated that the blocks of this invention be made by use of an endless conveyor chain to which is attached a multiplicity of individual molds. The molds would be of rectangular cross section with a width of no more than about three inches. The length and depth of the mold would be several times the width. Molten DMT (temperature about 145° C.) would be fed into the individual molds through a dispensing nozzle. Preferably, the dispensing nozzle and the mold would be blanketed by an inert gas during the mold filling step. The filled mold would then be conveyed through a quenching bath maintained at a temperature well below the melting point of DMT. After solidification of the DMT the molds would be conveyed out of the quenching bath and inverted to cause the solid DMT to fall from the mold. The now-empty mold would then be conveyed back to the dispensing nozzle to repeat the cycle.

We claim:

1. A block of dimethylterephthalate having needle-like crystals extending inwardly from all exterior surfaces, a uniform chemical analysis, a maximum thickness of three inches, and being easily cleavable without excessive dusting.

2. The block of dimethylterephthalate of claim 1 which has two substantially parallel oppositely disposed planar surfaces that are separated by a maximum of about three inches.

3. The block of claim 2 in which needle-like crystals extend inwardly from each of the substantially parallel oppositely disposed planar surfaces, and the needle-like crystals from the substantially parallel oppositely disposed planar surfaces fill substantially the entire volume between said planar surfaces.

4. The block of claim 3 in which the needle-like crystals from the substantially parallel oppositely disposed planar surfaces meet and form an optically apparent crystal interruption line that may be observed by cleaving the block at a right angle to the planar surfaces.

5. The block of claim 1 having an orthorhombic shape, i.e., the block has three axes of different lengths that intersect at right angles.

* * * * *